(12) United States Patent
Jamieson et al.

(10) Patent No.: US 10,285,605 B2
(45) Date of Patent: ***May 14, 2019

(54) INTEGRATED OPTICAL NEURAL PROBE

(71) Applicant: DIAGNOSTIC BIOCHIPS, INC.,
Glen Burnie, MD (US)

(72) Inventors: Brian Jamieson, Severna Park, MD (US); Jennette Mateo, Columbia, MD (US)

(73) Assignee: DIAGNOSTIC BIOCHIPS, INC., Glen Burnie, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/716,906

(22) Filed: Sep. 27, 2017

(65) Prior Publication Data

US 2018/0028119 A1 Feb. 1, 2018

Related U.S. Application Data

(63) Continuation of application No. 13/190,441, filed on Jul. 25, 2011, now Pat. No. 9,801,559.

(51) Int. Cl.
*A61B 5/04* (2006.01)
*A61B 5/0478* (2006.01)
(Continued)

(52) U.S. Cl.
CPC ........ *A61B 5/04001* (2013.01); *A61B 5/0084* (2013.01); *A61B 5/6848* (2013.01);
(Continued)

(58) Field of Classification Search
CPC .................................................. A61B 5/04001
See application file for complete search history.

(56) References Cited

U.S. PATENT DOCUMENTS 6,304,784 B1 10/2001 Allee et al.
7,010,356 B2 3/2006 Jog et al.
(Continued)

FOREIGN PATENT DOCUMENTS

WO WO2011/047381 A1 4/2011
WO WO2011/068696 A2 6/2011
WO WO2011/068696 A3 6/2011

OTHER PUBLICATIONS

Mancuso, J., et al., "Optogenic probing of functional brain circuitry," Experimental Physiology, Nov. 5, 1010, pp. 26-22, vol. 96-1, The Physiological Society.
(Continued)

*Primary Examiner* — Lee S Cohen
(74) *Attorney, Agent, or Firm* — Cermak Nakajima & McGowan LLP; Malcolm K. McGowan

(57) ABSTRACT

In certain embodiments, a neural probe comprises a substrate comprising elongated shanks for penetrating neural tissue, each comprising a proximal end and a distal end; at least one optical source integral to the neural probe for illuminating the neural tissue; and microelectrodes located proximate the distal end of the elongated shanks for monitoring neuronal activity. In certain embodiments, a method of monitoring neuronal activity comprises implanting the neural probe into a test subject such that the elongated shanks protrude into neural tissue of the test subject; illuminating the neural tissue with the at least one optical source; and measuring neuronal activity in response to illuminating the neural tissue. In certain embodiments, a device comprises a semiconductor chip; at least one optical source integral to the semiconductor chip; and sensor elements integral to the semiconductor chip for collecting data responsive to light emitted from the at least one optical source.

10 Claims, 5 Drawing Sheets

(51) Int. Cl.
A61B 5/00 (2006.01)
A61N 5/06 (2006.01)
A61B 18/22 (2006.01)

(52) U.S. Cl.
CPC .......... *A61B 5/6868* (2013.01); *A61N 5/0622* (2013.01); *A61B 2018/2266* (2013.01); *A61B 2018/2272* (2013.01); *A61B 2562/046* (2013.01); *A61N 2005/065* (2013.01); *A61N 2005/0612* (2013.01)

(56) References Cited

U.S. PATENT DOCUMENTS

| | | | |
|---|---|---|---|
| 8,263,986 | B2 | 9/2012 | Hajj-Hassan et al. |
| 9,247,889 | B2 | 2/2016 | Yoon |
| 9,801,559 | B2 * | 10/2017 | Jamieson et al. .. A61B 5/04001 |
| 2002/0028990 | A1 | 3/2002 | Shepherd et al. |
| 2008/0077198 | A1 | 3/2008 | Webb et al. |
| 2008/0077200 | A1 | 3/2008 | Bendett et al. |
| 2009/0177144 | A1 | 7/2009 | Masmanidis et al. |
| 2010/0292546 | A1 | 11/2010 | Gonopolskiy et al. |
| 2010/0292758 | A1 | 11/2010 | Lee et al. |
| 2011/0087311 | A1 | 4/2011 | Zorzos et al. |
| 2011/0112591 | A1 | 5/2011 | Seymour et al. |
| 2011/0144723 | A1 | 6/2011 | Streeter et al. |
| 2011/0208031 | A1 | 8/2011 | Wolfe et al. |
| 2012/0172952 | A1 | 7/2012 | Yoon et al. |
| 2013/0030274 | A1 | 1/2013 | Jamieson et al. |

OTHER PUBLICATIONS

Aravanis, A., et al., "An optical neural interface: in vivo control of rodent motor cortex with integrated fiberoptic and optogenic technology," Journal of Neural Engineering, Jun. 1, 2007, 7 J. Nurel Eng. 4 S143-S156.

U.S. Appl. No. 61/248,714, filed Oct. 8, 2009, 21 pages.

Zorzos, A., et al., "Multiwaveguide implantable probe for light delivery to sets of distributed brain targets," Optics Letters, Dec. 15, 2010, pp. 4133-4135, vol. 35, No. 24.

Zhang, J., et al., "Optical Control of Neural Activity by Waveguide Delivery in Genetically Targeted Brain Tissue," 2009, OSA/CLEO/IQEC, Providence, Rhode Island, 2 pages.

Kobayashi, R., et al., "Development of Si Neural Probe with Optical Waveguide for Highly Accurate Optical Stimulation of Neuron," Proceedings of the 5th International IEEE EMBS Conference on Neural Engineering, May 1, 2011, pp. 294-297.

Tanghe, S., et al., "A 16-Channel CMOS Neural Stimulating Array," Circuits for Transducers and Ative-Matrix LCD Drivers Paper 7.6, Feb. 20, 1992, ISSCC 92 Session 7, pp. 128-129.

Im, M., et al., "Neural Probes Integrated with Optical Mixer/Splitter Waveguides and Multiple Stimulation Sites," MEMS 2001, Jan. 27, 2011, pp. 1051-1054.

Mateo, J., et al., "Neural probes with waveguides and a fiber-coupled light emitting diode," Center for Nanoscale Science & Technology, NIST 2010 Reports, Dec. 31, 2010, pp. 68-69.

Cho, I., et al., "A 16-Site Neural Probe Integrated with a Waveguide for Optical Stimulation," Micro Electro Mechanical Systems (MEMS), 2010 IEEE 23rd International Conference on, IEEE, Piscataway, NJ, Jan. 24, 2010, pp. 995-998.

Zhang, J., et al., "Integrated device for optical stimulation and spatiotemporal electrical recording of neural activity in light-sensitized brain tissue," Journal of Neural Engineering, Sep. 1, 2009, 2009 J. Neural Eng. 6, pp. 1-13.

Royer, S., et al., "Multi-array silicon probes with integrated optical fibers: light-assisted perturbation and recording of local neural circuits in the behaving animal," European Journal of Neuoscience, col. 31, pp. 2279-2291.

International Search Report and Written Opinion of the International Searching Authority dated Oct. 9, 2012, for International Application No. PCT/US12/47997 filed on Jul. 24, 2012.

Extended European Search Report for European Patent App. No. 12818177.3 (dated Apr. 10, 2015).

He, X., et al., "Effects of parylene C layer on high power light emitting diodes," Appl. Surface Sci. 2009;256(1):6-11.

Communication Pursuant to Article 94(3) EPC for European Patent App. No. 12818177.3 (dated Aug. 6, 2018).

* cited by examiner

INTEGRATED OPTICAL NEURAL PROBE

CROSS-REFERENCE TO RELATED APPLICATION

This application is a continuation of U.S. application Ser. No. 13/190,441, filed Jul. 25, 2011, now U.S. Pat. No. 9,801,559.

BACKGROUND OF THE INVENTION

Technical Field of the Invention

Implementations consistent with the principles of the invention generally relate to the field of integrating optical sources into semi-conductor based point-of-care medical diagnostic and test equipment, more specifically to systems and methods for integrating optical sources in neural probes.

Background

Timely medical diagnosis historically has been hampered by the limited ability of medical professionals to conduct various medical tests at the point of care. Patients often have visited their doctor, only to be sent to a separate lab facility to have blood work or other diagnostic tests conducted. Diagnosis of the patient was then delayed to wait for the lab results to be returned to the doctor for an informed diagnosis of the patient's condition. The size, cost, complexity, and diversity of medical test equipment needed to properly diagnose the full range of medical conditions to which the medical professional may be exposed has limited the amount of point of care diagnostic equipment available to the typical medical professional.

Thus there is a need in the art for cost effective point of care medical diagnostic systems that can be used by the typical medical professional.

Certain medical diagnostic devices require a light source to conduct their tests. Example devices include pulse oximeters, flow cytometers, DNA sequencers, and immunoassays. A pulse oximeter is a clinical device that uses the differential absorption of visible (red) and infrared light by hemoglobin to detect changes in blood oxygenation. A flow cytometer uses scattering or other optical information from fluorescently-labeled cells to count and otherwise quantify the type and quantity of cells in a sample. DNA sequencing relies on a variety of analytical and chemical techniques, however the detection of processed DNA strands is often accomplished with a fluorescent or other optical signal. Finally, an immunoassay uses the competitive binding of an antibody to detect the concentration of an analyte of interest in a sample. Detection of the antibody/antigen binding can be done in a variety of ways, but is often accomplished with optical methods such as fluorescent detection. Typically the light sources utilized in these and other similar devices have led to large, cumbersome test devices to connect the light source, power source, control electronics, and other data or sample collecting sensors. This size and complexity has added to the expense of these diagnostic devices and limited their use at point of care.

There is thus a need in the art to integrate optics into portable point of care medical diagnostic devices to reduce the cost, size and complexity of such devices.

In addition, certain test devices must be implanted into a test subject to collect data. Neural probes are one such example. For example, it is known by those of skill in the art that directing light to a very localized and precise region of excitable neural tissue can be used to open ion channels that were previously implanted into the neural cells with genetic techniques, causing those channels to open and thus an action potential to fire. An action potential is a stereotyped voltage waveform that arises from ionic current across a cell membrane.

Various designs of neural probes have been attempted in the art to use these phenomena for test purposes. For example, silicon neural probes with an optical fiber glued to it in order to direct light to the very localized and precise region of excitable neural tissue have been attempted. Metal recording sites on the neural probe detected the electrical cell activity of the optically-triggered action potential. These devices required an external optical source and were extremely tedious to assemble and were thus expensive and demanding to build and operate. These shortcomings place such method and devices beyond the reach of most researchers of clinicians.

Some recent efforts at integrating the light delivery with the microelectrode have been reported, however these approaches rely on highly labor-intensive "one-off" assembly procedures in which optical fibers are etched and then manually aligned and attached to silicon recording arrays. Other groups have demonstrated probes with integrated waveguides, however the light sources (i.e. laser or LED) are bulky and are separate from the probe and connected by a fiber which is problematic for behavioral experiments.

There is a need in the art for a neural probe with integrated optical stimulation that allows implanting the probes without a tether, and enables the selective stimulation and monitoring of neuronal activity in freely behaving animals.

There further is a need in the art for a neural probe with an integral optical source to simplify the performance of experiments in which it is desired to optically stimulate a targeted set of neurons while accurately recording responses from those and other neurons.

There further is a need in the art to integrate one or more optical sources in a neural probe to facilitate implanting the neural probe in an animal or human test subject.

SUMMARY OF THE INVENTION

Various systems and methods relating to integrating optical sources in semi-conductor based medical devices are disclosed and claimed.

In certain embodiments, a neural probe, comprises a substrate comprising one or more elongated shanks for penetrating neural tissue, each elongated shank comprising a proximal end and a distal end; at least one optical source integral to the neural probe for illuminating the neural tissue; and one or more microelectrodes located proximate the distal end of one or more of the elongated shanks for monitoring neuronal activity. The neural probe may further comprise readout circuitry electrically connected to the one or more microelectrodes. The readout circuitry may comprise one or more readout electrodes electrically connected to the one or more microelectrodes. The neural probe may further comprise a power source integral to the neural probe and electrically connected to the at least one optical source. The neural probe may further comprise a coupler for coupling the at least one optical source to at least one waveguide. The coupler may couple each of the at least one optical source to a plurality of optical fibers. The one or more conductive microelectrodes may be lithographically printed on one or more of the elongated shanks. The at least one optical source may be located proximate the distal end of the one or more elongated shanks to illuminate the neural tissue without an optical waveguide. The neural probe may further comprise at least one of a lens, a reflector and a grating for directing the light from the at least one optical source to illuminate the neural tissue. The at least one optical source may comprise at least one of an LED, a photonic crystal light source, a quantum dot and a laser. The neural probe may further comprise at least one optical waveguide connecting the at least one optical source to the one or more microelectrodes. The neural probe may further comprise at least one of a lens, a reflector and a grating for directing the light from the at least one optical source to the at least one optical waveguide. The neural probe may further comprise at least one of a lens, a reflector and a grating for directing the light from the at least one optical waveguide to illuminate the neural tissue. The at least one optical source may be flip chip bonded to the silicon substrate. The at least one optical source may be integrated with the neural probe by silicon microfabrication.

In certain embodiments, a method of monitoring neuronal activity comprises implanting any of the variations of neural probes discussed above into a test subject such that the one or more elongated shanks protrude into neural tissue of the test subject; illuminating the neural tissue with the at least one optical source; and measuring neuronal activity in response to illuminating the neural tissue. The method may further comprise transmitting the measured neuronal activity to an analysis unit remote from the test subject. The test subject may a selected one of an animal and a human.

In certain embodiments a device comprises a semiconductor chip; at least one optical source integral to the semiconductor chip; and one or more sensor elements integral to the semiconductor chip for collecting data responsive to light emitted from the at least one optical source. The semiconductor chip may comprise a substrate comprising one or more elongated shanks for penetrating neural tissue, each elongated shank may comprise a proximal end and a distal end; and/or the one or more sensor elements may comprise one or more microelectrodes located proximate the distal end of one or more of the elongated shanks for monitoring neuronal activity.

Other aspects and advantages of the present invention may be seen upon review of the figures, the detailed description, and the claims that follow.

BRIEF DESCRIPTION OF THE DRAWINGS

Some embodiments of the invention are described with reference to the following figures.

DETAILED DESCRIPTION

Figure 1:
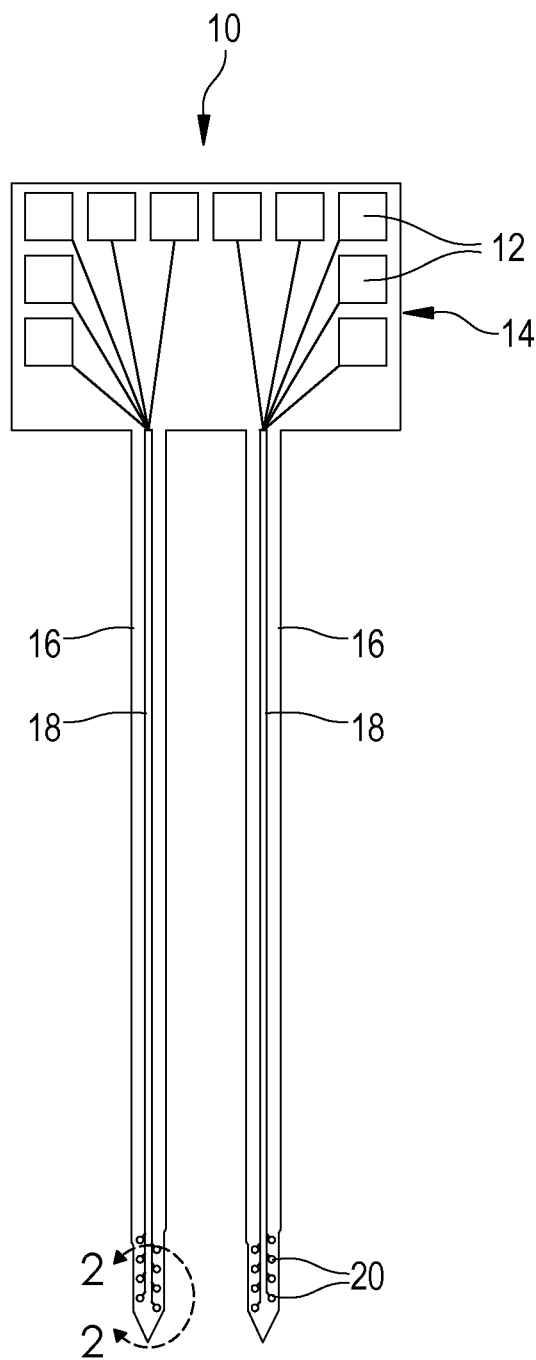
FIG. 1 is a top view of a neural probe according to certain embodiments of the invention.

Certain embodiments of the invention relate to systems and methods for integrating optical sources in highly miniaturized systems such as point of care medical diagnostic and analytical test equipment, biosensors, bioMEMS, and other implantable devices. Certain embodiments of the invention also relate to methods for integrating optical sources into therapeutic and combined diagnostic/therapeutic devices. An example of a therapeutic device is a neural stimulator, for example for the treatment of Parkinson's Disease, and an example of a combined diagnostic/therapeutic device is an endoscope or catheter.

Certain embodiments of the invention allow the application of a spatially and temporally selective optical stimuli to a very small volume of tissue, solution or other material, and the subsequent or simultaneous measurement of the electrical, chemical, or other response elicited by the application of the optical stimulus. In certain embodiments, a neural probe device allows the delivery of blue or other wavelength light to small volumes of neural tissue containing channelrhodopsin (CHR2) ion channels, and then the measurement of action and field potentials resulting from that stimulus. In certain embodiment, the measured result of the optical stimulus might be the release or activation of a chemical compound such as a neurotransmitter, which can be detected by the chemical modification of the electrical recording sites found on the aforementioned neural probe. In certain related embodiments, the light could be delivered to a cell-containing solution, a culture, or a tissue slice, and the measured response could again be electrical or chemical in nature. In one embodiment, the solution might be introduced to the device through microfluidic channels or chambers contained therein, or cells could be cultured on the device itself. In another embodiment, light sensitive dies or fluorescent molecules contained in the solution or bound on the surface of the microdevice could be interrogated by the optical source, and the electrical or chemical readout could be accomplished by recording sites in proximity to the optical source. For example, it may be beneficial to implement a novel flow cytometer that operates by passing a sample of blood cells through a narrow channel into which light is delivered. In certain embodiments, if certain subclasses of cells were tagged with an optically-sensitive channel protein, the light trigger would elicit a change in membrane potential that could be detected by the integrated recording sites (microelectrodes.) in certain embodiments, the development of a biosentinel device in which a living cell culture is intentionally introduced onto or into a microfluidic or "lab-on-a-chip" device. The normal behavior of a particular neuronal circuit, or the presence of "normal" electrical cellular behavior could be monitored subsequent to periodic optical interrogation. Changes to the measured response could then be used to elicit information about the presence of bioactive agents or other toxins. A nerve gas detector, for example, might utilize a neuronal cell culture with known high sensitivity to nerve gas. The neurons, cultured with ChR2 or other appropriate channel proteins, would be a "canary in a coal mine," by exploiting the very high signal gain of membrane proteins in transducing a chemical signal to a voltage signal. This coupled chemical/optical/electrical system is one embodiment of the subject invention; other biosensors are known to those of ordinary skill in the art. In certain embodiments for highly localized characterization of photovoltaic materials, the optical probe/electrical recording configuration could be used to locally stimulate a photovoltaic structure and measure the resulting response.

The present invention overcomes the shortcomings of the prior art described above and provides for implantable neural probe systems and methods for optically stimulating targeted neurons and recording multi-cell neuronal activity by integrating at least one optical source into the neural probes. Using an implantable integrated microsystem to modulate neuronal activity with optical stimulation and to simultaneously record single unit action potentials is a potentially groundbreaking approach to systems neurophysiology.

The at least one integral optical source can be used to direct light to a very localized and precise region of excitable neural tissue can be used to open ion channels that were previously implanted into the neural cells with genetic techniques, causing those channels to open and thus an action potential to fire.

Optical sources suitable for integration with diagnostic medical devices and test equipment in the present invention, including but not limited to the certain embodiments depicted in the above figures and described more fully below, include without limitation LEDs, lasers, quantum dots and photonic crystal light sources. There are various methods for producing a compact and energy efficient light source suitable for integration into a microsystem. LED's can be constructed of a III-V semiconductor such as GaN, InP, AlGaN, or others. These materials can be deposited on a sapphire, silicon, or other substrate through molecular beam epitaxy, chemical vapor deposition, or another technique. Organic LED's can be deposited as a multi-layer device through thermal evaporation or spin-casting, and offer the advantage of simple and cost effective integration with other semiconductor processing techniques. Techniques for integrating compact lasers (electrically pumped diodes) into semiconductor devices are well-known, and these devices include VECSELS, VCSELS, quantum cascade lasers and others. Such optical sources can in some cases be built on a silicon substrate and thus integrated with semiconductor fabrication processes such as those used to fabricate silicon neural probes. As an alternative, quantum dots may be fabricated on a substrate surface by molecular beam epitaxy (MBE), through electrochemical methods, or through other fabrication techniques known to those skilled in the art.

One of ordinary skill in the art will recognize that integral optical sources may be integrated with a neural probe by flip chip bonding, silicon microfabrication, and other methods know to those of ordinary skill in the art.

In certain embodiments, an organic LED (OLED) may be fabricated on the wafer containing partially completed neural probes, following the fabrication of shanks, sites, interconnect, dielectric isolation and other important features of the probes, but prior to their being released from the wafer into free-standing devices. The fabrication steps necessary to spin cast OLED's are described elsewhere and these steps can be integrated into the normal course of wafer processing. The OLED's would be patterned lithographically in order to produce integrated sources on the body of the neural probe or other device. The OLED could be controlled (turned on and off, adjusted in intensity) and monitored via electrical leads that connect to it from the readout portion of the neural probe or other device.

In certain embodiments, an optical source may be integrated with the wafer substrate containing neural probes through flip chip bonding. This step may be carried out at any point in the fabrication process, depending on the specifics of probe release (yield) efficiency and other process issues. In this case, the optical source may be attached to the substrate in a precise alignment and attach process that utilizes some combination of heat, pressure and ultrasonic energy to cause a permanent bond between the source and the wafer substrate. This step could be carried out in a highly parallel manner, with many sources being attached to neural probes prior to their release from the substrate wafer.

FIG. 1 shows a neural probe 10 in accordance with certain embodiments of the present invention. Neural probe 10 may comprise a semiconductor substrate, which may comprise one or more elongated shanks 16 for penetrating neural tissue and a back end 14 at a proximal end of one or more elongated shanks 16. The back end 14 may comprise one or more bond pads 12 for electrically connecting to a plurality of recording sites 20 at a distal end of the one or more elongated shanks 16 by one or more electrically conductive interconnects 18. The interconnects 18 and recording sites 20 may comprise a conductive material, which may include one or more metals including but not limited to gold, iridium, or platinum.

Figure 2:
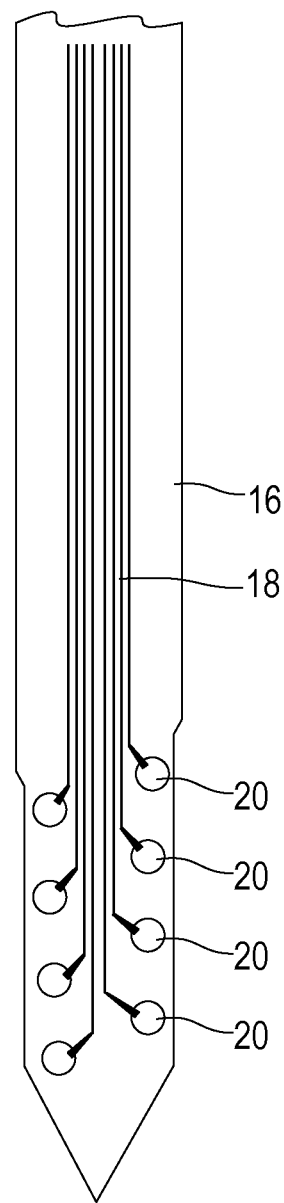
FIG. 2 is a top view of a recording site area of a neural probe according to certain embodiments of the invention.

FIG. 2 shows an expanded view of the distal end of an elongated shank 16 of neural probe 10 in accordance with certain embodiments of the present invention showing the elongated shank 16, the interconnects 18, and the recording sites 20 in greater detail.

Figure 3A:
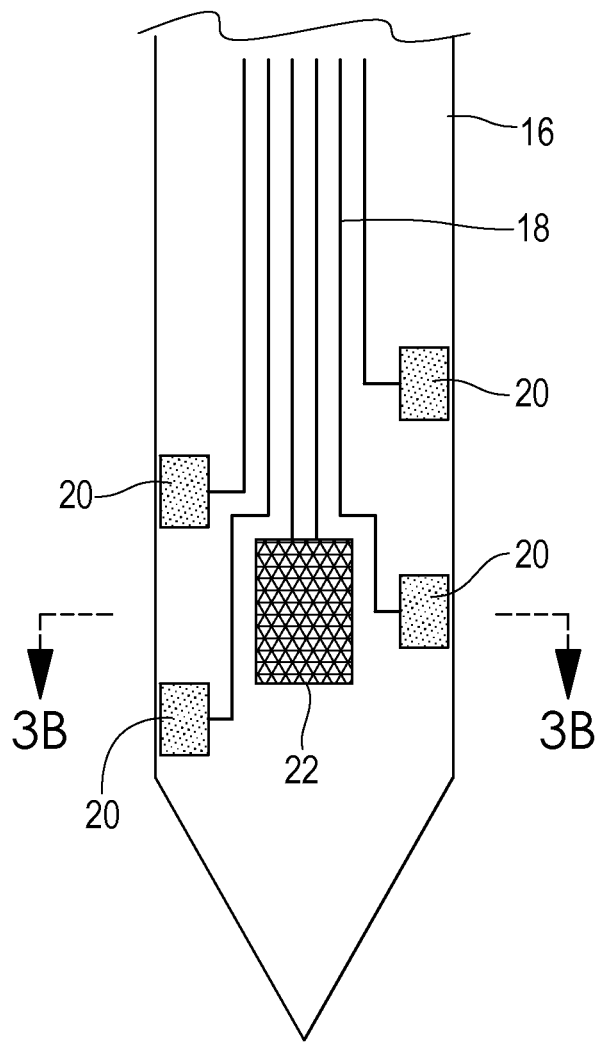
FIG. 3A is a top view of a recording site area of a neural probe including an integral optical source according to certain embodiments of the invention.

FIG. 3A shows an expanded view of the distal end of an elongated shank 16 of neural probe 10 including an integral optical source 22 in accordance with certain embodiments of the present invention. At least one integral optical source 22 may be located proximate the distal end of one or more elongated shanks 16, which for the purposes of the present invention means close enough to the distal end of one or more elongated shanks 16 that a waveguide is not required to direct the light emitted by the integral optical source to the neural tissue of interest. One of ordinary skill in the art will recognize that one or more lens, reflectors, gratings, or other optical components known to those of ordinary skill in the art may be used in conjunction with the at least one integral optical source 22 to focus the light emitted from the at least one integral optical source 22 to precisely and selectively excite the neural tissue of interest.

Figure 3B:
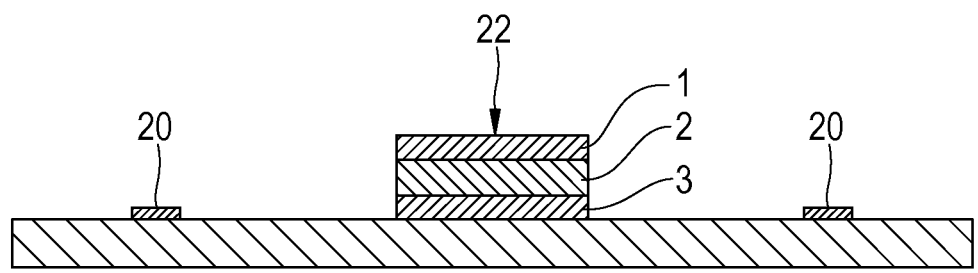
FIG. 3B is a cross-sectional view along line 3B-3B of the neural probe of FIG. 3 of a recording site area of a neural probe including an integral optical source according to certain embodiments of the invention.

FIG. 3B shows a cross sectional view of at least one integral optical source 22 which may be located proximate the distal end of one or more elongated shanks 16 as shown in FIG. 3A. The integrated optical source 22 may be located proximate at least one recording site 20. The integrated optical source 22 may comprise a buffer layer 3, an active semiconductor layer 2, and a passivation layer 1. The semiconductor layer may comprise GaN or other suitable semiconductor known to those of ordinary skill in the art including but not limited to AlGaN, InP, SiC, GaAs, Si, diamond or other materials known to those of ordinary skill in the art. In the case of GaN, for example, which is useful for producing a green light source, the material is typically deposited using metal organic chemical vapor deposition (MOCVD). A buffer layer is used between the deposited GaN layer and the silicon (or other) wafer substrate in order to account for the crystal mismatch between Si and GaN. In certain embodiments, the optical source may be an organic LED which is fabricated on the substrate surface through spin casting or thermal evaporation. In these embodiments, a buffer layer is not needed, however other layers pertinent to this device and known to those skilled in the art (e.g. a hole injection layer) are needed. The process for fabricating OLED's is well known by those skilled in the art. In all cases, the fabricated LED should be encapsulated with a thin film or other encapsulation layer, preferably one that is largely transparent, such as oxynitride or parylene, in order to allow robust functioning in vivo or in a moist environment such as a chemical solution.

Figure 4:
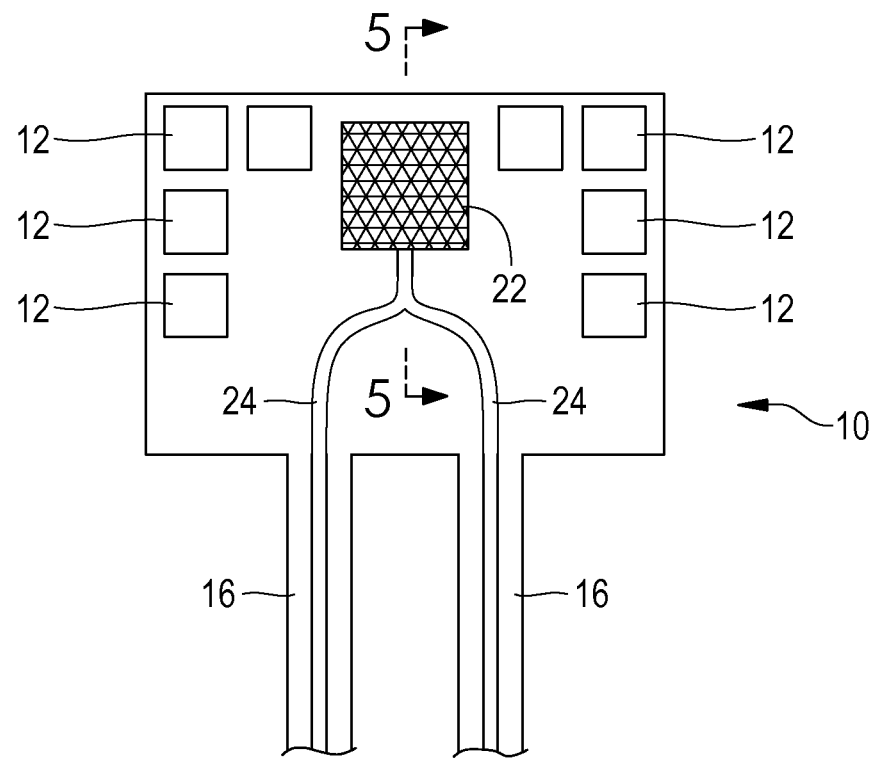
FIG. 4 is a top view of a back end of a neural probe including an integral optical source according to certain embodiments of the invention.

FIG. 4 shows an expanded view of a back end 14 of a neural probe 10 according to certain embodiments of the invention. The neural probe 10 comprises at least one integral optical source 22 integrated to the back end 14 of neural probe 10. Light emitted from the at least one integral optical source 22 may be directed to the distal end of one or more elongated shanks 16 to selectively illuminate neural tissue of interest by at least one waveguide 24. The back end 14 may comprise circuitry for amplifying the signal, buffering it and may perform more sophisticated functions including without limitation spike detection, multiplexing, and other signal processing functions known to those of ordinary skill in the art. The circuitry may provide power, control and/or monitor the at least one integral optical source 22. The circuitry may be integrated with the back end 14 through additional semiconductor processing steps that create the CMOS circuitry in the same way that this is done in industry standard, except that the circuitry is integrated with the semiconductor substrate of the back end 14 of neural probe 10.

Figure 5:
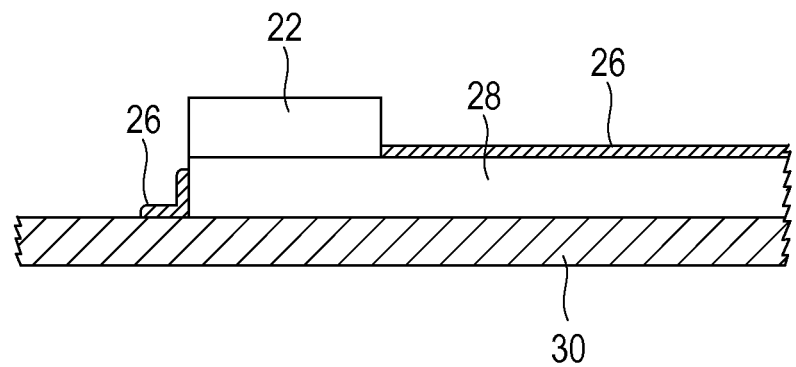
FIG. 5 is a cross section view along line 5-5 of the neural probe of FIG. 4 according to certain embodiments of the invention.

FIG. 5 shows a cross sectional view of the embodiment of FIG. 4 along Section 5-5. At least one integral optical source 22 may be configured to selectively emit light into at least one waveguide 28 formed by probe substrate 30 and cladding 26. Probe substrate 30 and cladding 26 may be substantially opaque to prevent the escape of significant quantities of the emitted light. The waveguide 28 may direct the emitted light from the at least one integral optical source 22 located at the back end 14 of neural probe 10 to the distal end of one or more elongated shanks 16 to selectively illuminate neural tissue of interest.

Figure 6:
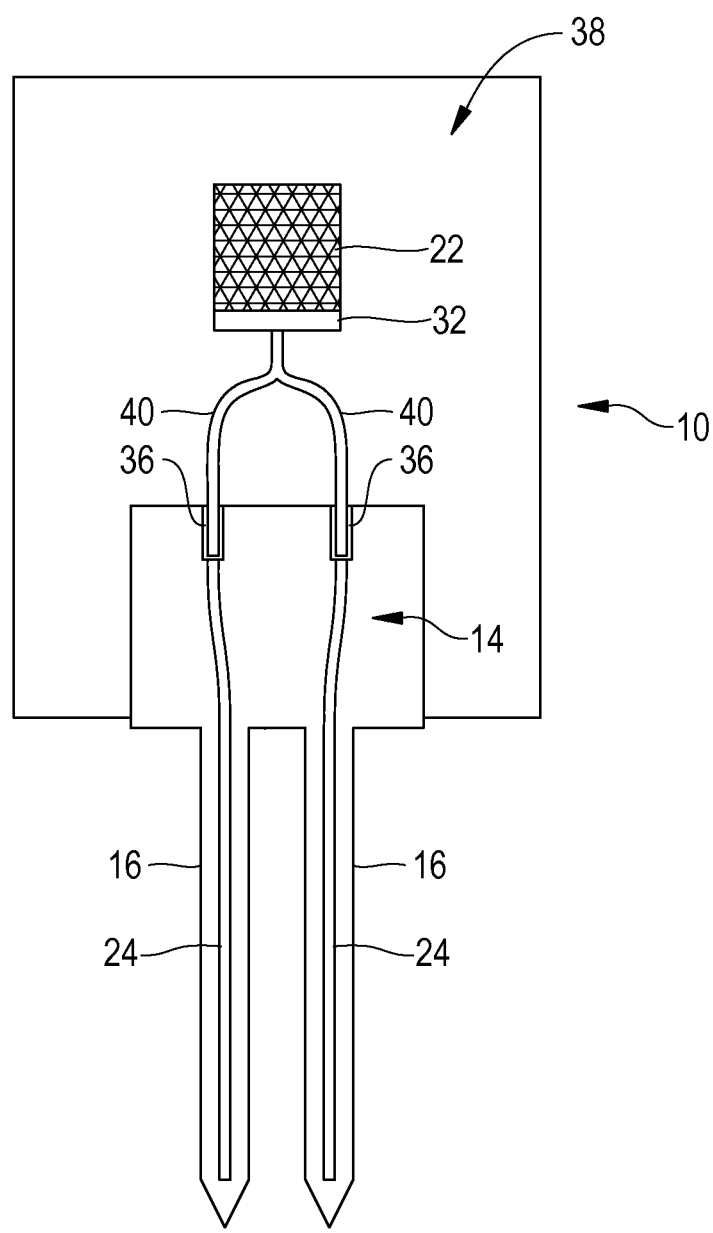
FIG. 6 is a top view of a neural probe according to certain embodiments of the invention.

FIG. 6 shows a neural probe 10 in accordance with certain embodiments of the present invention. Neural probe 10 may comprise a semiconductor substrate which may comprise a back end 14 and one or more elongated shanks 16. The semiconductor substrate may comprise silicon and may be fixedly attached to a head stage 38, which may comprise a printed circuit board. The head stage may comprise circuitry for amplifying the signal, buffering it and may perform more sophisticated functions including without limitation spike detection, multiplexing, and other signal processing functions known to those of ordinary skill in the art. The head stage may comprise at least one integral optical source 22, which may be optically coupled to a coupler 32. The coupler 32 may optically couple the at least one integral optical source 22 to a plurality of optical fibers 40. The plurality of optical fibers 40 may terminate at a plurality of etched alignment grooves on the back end 14 of the semiconductor substrate. Light emitted from the optical fibers 40 may be directed to neural tissue of interest by at least one waveguide 24 which may be optically coupled to the plurality of optical fibers 40. One of ordinary skill in the art will recognize that light emitted by the at least one integral optical source 22 may be optically coupled directly to the at least one waveguide 24 without departing the scope of the invention.

Figure 7A:
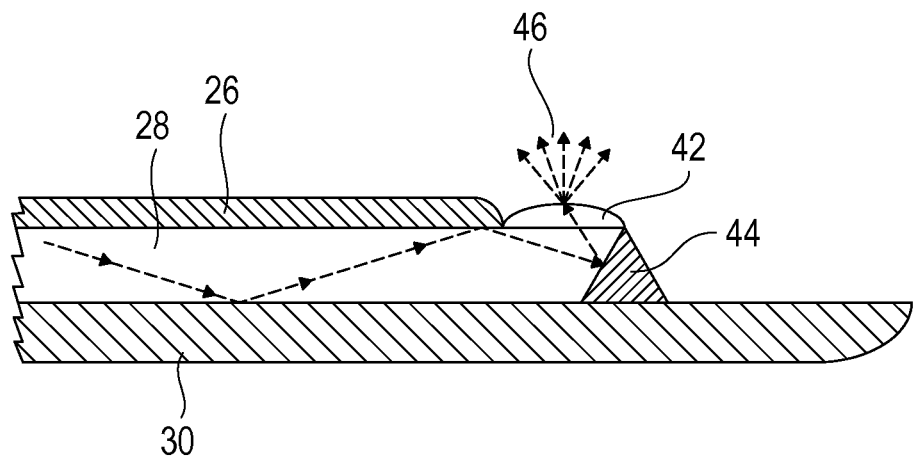
FIGS. 7A and B are sides view of portions of an elongated shank of a neural probe according to certain embodiments of the invention.
Figure 7B:
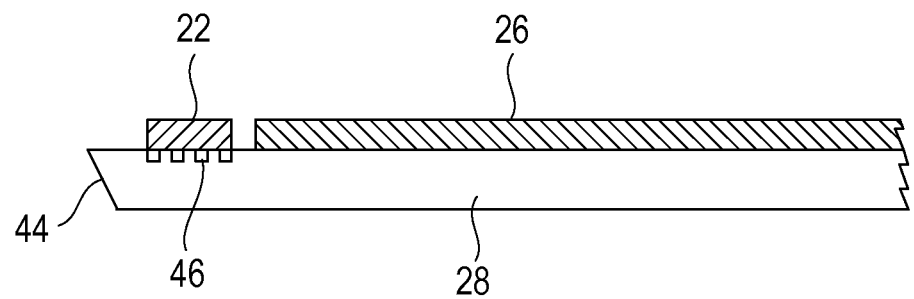

FIGS. 7A and 7B show various means to shape the profile and/or increase the efficiency of light emitted coupled from integral optical sources that may also be integrated into a neural probe according to certain embodiments of the invention.

FIG. 7A shows a waveguide 28 for directing light from at least one optical source 22 to neural tissue of interest according to certain embodiments of the invention. The waveguide 28 may be formed by semiconductor substrate 30 and cladding 26. The neural probe may further comprise a reflector 44 and/or a lens 42 which may be used to shape the profile and/or increase the efficiency of emitted light 46 to selectively illuminate neural tissue of interest.

FIG. 7B shows a waveguide 28 for directing light from at least one optical source 22 to neural tissue of interest according to certain embodiments of the invention. For example, the certain embodiments shown in FIG. 7B may be applicable, without limitation, to direct light from at least one optical source 22 integrated at the back end 14 of neural probe 10. One or more of reflector 44, grating 46 and waveguide 28 may be used to shape the profile and/or increase the efficiency of light emitted coupled from at least one integral optical source 22 to deliver the shaped emitted light to neural tissue of interest.

One of ordinary skill in the art will recognize that a variety of combinations of integral light sources, waveguides, optical fibers, lens, gratings, and reflectors may be utilized without deviating from the scope of the invention and that the foregoing embodiments are exemplary and non-limiting.

One of skill in the art will recognize that the systems and methods of the invention, which are exemplified by but not limited to the foregoing embodiments, are equally applicable to any application which required the controlled and selective application of light to a very precise location. An exemplary application is the selective stimulation of small groups of neurons for the treatment of Parkinson's disease or another neurological disorder. Similarly, an integrated optical probe could be used for pace-making or otherwise selectively activating cardiac cells or other electroactive cells in the heart, gastrointestinal tract, or anywhere else in the body. A microfluidic device incorporating the proposed invention could be used to selectively activate cells in a culture which was intentionally incorporated into the device, either for scientific study or for the development of a sentinal device for biodetection. For example, a microfluidic device with cultured neurons that are highly sensitive to a certain toxin could be used as a biosensor. The neurons, with Channelrhodopsin (ChR2) or other light-sensitive channels incorporated into them, could be periodically optically-interrogated by the microfluidic device to confirm that the neuronal circuit is still responsive and thus has not been compromised by the presence of the toxin of interest.

Test Results

Using an implantable integrated microsystem to modulate neuronal activity with optical stimulation and to simultaneously record single unit action potentials is a potentially groundbreaking approach to systems neurophysiology. The inventors are working to produce highly integrated electrodes that can be used in studies of learning, memory and brain plasticity. When excitable cells with a genetically-expressed protein called Channelrhodopsin (ChR2) are exposed to blue light (480 nm), neuronal action potentials are triggered in these cells. Light is typically delivered using a laser or an LED coupled to an optical fiber and the electrical signals are probed using an independent microelectrode. Some recent efforts at integrating the light delivery with the microelectrode have been reported, however these approaches rely on highly labor-intensive "one-off" assembly procedures in which optical fibers are etched and then manually aligned and attached to silicon recording arrays. Other groups have demonstrated probes with integrated waveguides, however the light sources (i.e. laser or LED) are bulky and are separate from the probe and connected by a fiber which is problematic for behavioral experiments. Designing a neural probe with integrated optical stimulation allows implanting the probes without a tether, and enables the selective stimulation and monitoring of neuronal activity in freely behaving animals.

MEMS silicon neural probes with integrated waveguides may be fabricated with a bulk micromachined silicon-on-insulator process. A top dielectric stack of stress balanced oxide-nitride-oxide layers may provide hermeticity from the tissue during implantation. Recording sites may be patterned from platinum or iridium, which can subsequently be oxidized to reduce site impedance. U-grooves may be wet etched where the optical fiber is to be fixed, and an SU8, oxynitride or other waveguide is patterned. Probe boundaries may be etched with DRIE, and a second patterned DRIE backside etch may be used to release the probes from the wafer. An LED coupled to four optical fibers may be fixed on a small headstage (printed circuit board), with fiber ends aligned in the V-grooves to the SU8 waveguides.

A coupler that connects a high intensity LED (XRE Cree XLamp) to four optical fibers has been designed, constructed and tested. The coupler is made of ceramic, stainless steel and brass, and may be fixed onto the LED using a UV-curable adhesive. The optical power values measured using a Thorlabs PM100A power meter at the end of each fiber were found to be practically equal (+−12%) across the four fibers.

Passive neural probes (e.g. probes without optical stimulation) fabricated using the bulk micromachined SOI process described above are currently being used in behavioral experiments. The integration of optical elements onto these devices represents an opportunity for a system-level approach that will accelerate experimental progress in this area.

More generally, the present invention may have applications to the integration of advanced functionality (CMOS circuitry, optical sources and detectors, acoustic sources and other actuators) into MEMS and microfluidic systems. The development of highly integrated and functional Biomedical Microsystems has been enabling the development of highly miniaturized, low power and capable systems for biomedical applications.

Improved methods of optical source integration including the flip chip bonding of an LED to the silicon probe substrate, as well as the integration of OLED and other LED's directly into the probe process flow are currently under development by the inventors.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit, and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

We claim:

1. A neural probe, comprising:
   a semiconductor substrate comprising a back end and one or more elongated shanks for penetrating neural tissue, each elongated shank comprising a proximal end and a distal end;
   at least one optical source integral to the neural probe for illuminating the neural tissue,
   wherein the optical source is located proximate the distal end of one or more elongated shanks such that, when the probe is implanted, the neural tissue may be illuminated without the use of an optical waveguide; and
   one or more conductive microelectrodes located proximate the distal end of one or more of the elongated shanks for monitoring neural activity,
   wherein the at least one optical source comprises a buffer layer, an active semiconductor layer comprising a III-V semiconductor, and a passivation layer.

2. The neural probe of claim 1, further comprising readout circuitry electrically connected to the one or more microelectrodes.

3. The neural probe of claim 1, the back end further comprising a power source electrically connected to the at least one optical source.

4. The neural probe of claim 1, wherein the one or more conductive microelectrodes are lithographically printed on one or more of the elongated shanks.

5. The neural probe of claim 1, further comprising at least one of a lens, a reflector and a grating configured to direct light from the at least one optical source to illuminate the neural tissue.

6. The neural probe of claim 1, wherein the at least one optical source is a flip chip bonded to a silicon substrate.

7. The neural probe of claim 1, wherein the at least one optical source is integrated with the neural probe by silicon microfabrication.

8. A method of monitoring neuronal activity comprising:
   implanting the neural probe of claim 1 into a test subject such that the one or more elongated shanks protrude into neural tissue of the test subject;
   illuminating the neural tissue with the at least one optical source; and
   measuring neuronal activity with the microelectrodes in response to illuminating the neural tissue.

9. The method of claim 8, further comprising transmitting the measured neuronal activity to an analysis unit remote from the test subject.

10. The method of claim 8, wherein the test subject is a selected one of an animal and a human.

* * * * *